(12) United States Patent
Weldon (10) Patent No.: US 8,035,809 B2
(45) Date of Patent: Oct. 11, 2011

(54) BUBBLE REMOVAL SYSTEM

(75) Inventor: John P. Weldon, Honeoye Falls, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 280 days.

(21) Appl. No.: 12/325,353

(22) Filed: Dec. 1, 2008

(65) Prior Publication Data

US 2009/0161099 A1  Jun. 25, 2009

Related U.S. Application Data

(60) Provisional application No. 61/016,088, filed on Dec. 21, 2007.

(51) Int. Cl.
*G01N 21/00* (2006.01)

(52) U.S. Cl. .................. 356/239.2; 382/141
(58) Field of Classification Search .......... None
See application file for complete search history.

(56) References Cited

U.S. PATENT DOCUMENTS

| | | | | |
|---|---|---|---|---|
| 5,105,841 A * | 4/1992 | Oguma et al. | ............... | 134/57 R |
| 5,578,331 A * | 11/1996 | Martin et al. | ................. | 425/445 |
| 5,649,410 A * | 7/1997 | Martin et al. | ................. | 53/474 |
| 5,814,134 A * | 9/1998 | Edwards et al. | ............... | 96/6 |
| 6,113,817 A * | 9/2000 | Herbrechtsmeier et al. | . | 264/1.36 |
| 6,118,528 A * | 9/2000 | Yanagi | ................. | 356/246 |
| 6,134,342 A | 10/2000 | Doke et al. | | |
| 6,475,410 B1 * | 11/2002 | Nakagawa | ............... | 264/2.5 |
| 2002/0018735 A1 * | 2/2002 | Rossell | ................. | 422/128 |
| 2002/0182315 A1 * | 12/2002 | Heiler et al. | ............... | 427/162 |
| 2006/0132761 A1 * | 6/2006 | Hall | ............... | 356/244 |
| 2007/0139640 A1 * | 6/2007 | Biel et al. | ............... | 356/124 |

OTHER PUBLICATIONS

Fred Sense: How can I predict oxygen solubility in water? © 1997-2005  http://antoine.frostburg.edu/chem/senses/101/solutions/faq/predicting-DO.shtml.
Omega Engineering, Inc. Technical Dissolved Oxygen—The Fundamentals © 2006.

* cited by examiner

*Primary Examiner* — Gregory J Toatley
*Assistant Examiner* — Juan D Valentin
(74) *Attorney, Agent, or Firm* — John E. Thomas (57) ABSTRACT

A bubble removal system includes an inspection cell configured to receive an ophthalmic device and a volume of working fluid. The system also includes a vacuum device configured to form a substantially fluid-tight seal with the inspection cell and to direct a negative pressure to the volume of working fluid and the ophthalmic device within the inspection cell.

23 Claims, 3 Drawing Sheets

BUBBLE REMOVAL SYSTEM

CROSS-REFERENCE TO RELATED APPLICATIONS

This application claims the benefit of Provisional Patent Application No. 61/016,088 filed Dec. 21, 2007 which is incorporated by reference herein.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to equipment used to manufacture ophthalmic devices, and, in particular, to equipment used to manufacture contact lenses.

2. Description of Related Art

Soft hydrogel contact lenses have increased in popularity since they were first introduced in the 1970s. Such contact lenses are conventionally formed through a process in which the material used to make the lenses is placed between two halves of a casting mold, and the entire assembly is then cured to form the desired contact lens shape. After the curing process, the lens is removed from the casting mold and is immersed in a series of fluids to remove impurities therefrom. While still immersed in fluid, the lens is taken to an examination station where it is inspected for foreign particles, holes, and/or deformations caused by the manufacturing process.

Existing systems for the inspection of contact lenses typically include a camera, a viewing monitor, and a computer. The computer is configured to run lens examination software which assesses images of the lens during a lens inspection process. In examining the lens, the camera and, in particular, the software, can inspect the lens for the foreign particles, holes, and deformities discussed above. Such examination is typically done while the lens is submerged in a working fluid such as water, and the software can control the inspection system to reject a lens if such deformities are found thereon.

Although existing inspection systems have some utility in a contact lens production environment, reliance on such systems can result in a large number of false lens rejections during production. For example, the camera and, in particular, the camera software may not be capable of distinguishing a hole, a foreign particle, or other lens deformities from gas bubbles entrained in the working fluid and/or adhered to the surface of the lens. Bubbles can be formed by, for example, turbulent working fluid flow within the various systems used for impurity removal. The bubbles can be carried with the lens to the inspection system. Depending on the type of contact lens being examined and the throughput of the manufacturing line, false lens rejections caused by existing camera inspection systems can dramatically increase production costs and can severely hinder manufacturing efficiency.

Accordingly, the disclosed systems and methods are directed towards overcoming one or more of the problems set forth above.

SUMMARY OF THE INVENTION

In an exemplary embodiment of the present disclosure, a bubble removal system includes an inspection cell configured to receive an ophthalmic device and a volume of working fluid. The system also includes a vacuum device configured to form a substantially fluid-tight seal with the inspection cell and to direct a negative pressure to the volume of working fluid and the ophthalmic device within the inspection cell.

In another exemplary embodiment of the present disclosure, a method of removing bubbles formed in a volume of working fluid includes disposing an ophthalmic device within the volume of working fluid, the volume of working fluid being contained within an inspection cell. The method also includes forming a sealed region between the inspection cell and a vacuum device, directing a negative pressure to the sealed region with the vacuum device, and removing at least one bubble from the volume of working fluid.

In still another exemplary embodiment of the present disclosure, a method of preparing a volume of working fluid for the inspection of an ophthalmic device includes substantially submerging the ophthalmic device in the working fluid, reducing a pressure of the working fluid below an ambient pressure, and bringing a portion of the liquid to a boil. The method also includes increasing the pressure of the working fluid to the ambient pressure and sensing at least one characteristic of the ophthalmic device while the ophthalmic device is substantially submerged in the working fluid.

DETAILED DESCRIPTION OF THE DRAWINGS

Figure 1:
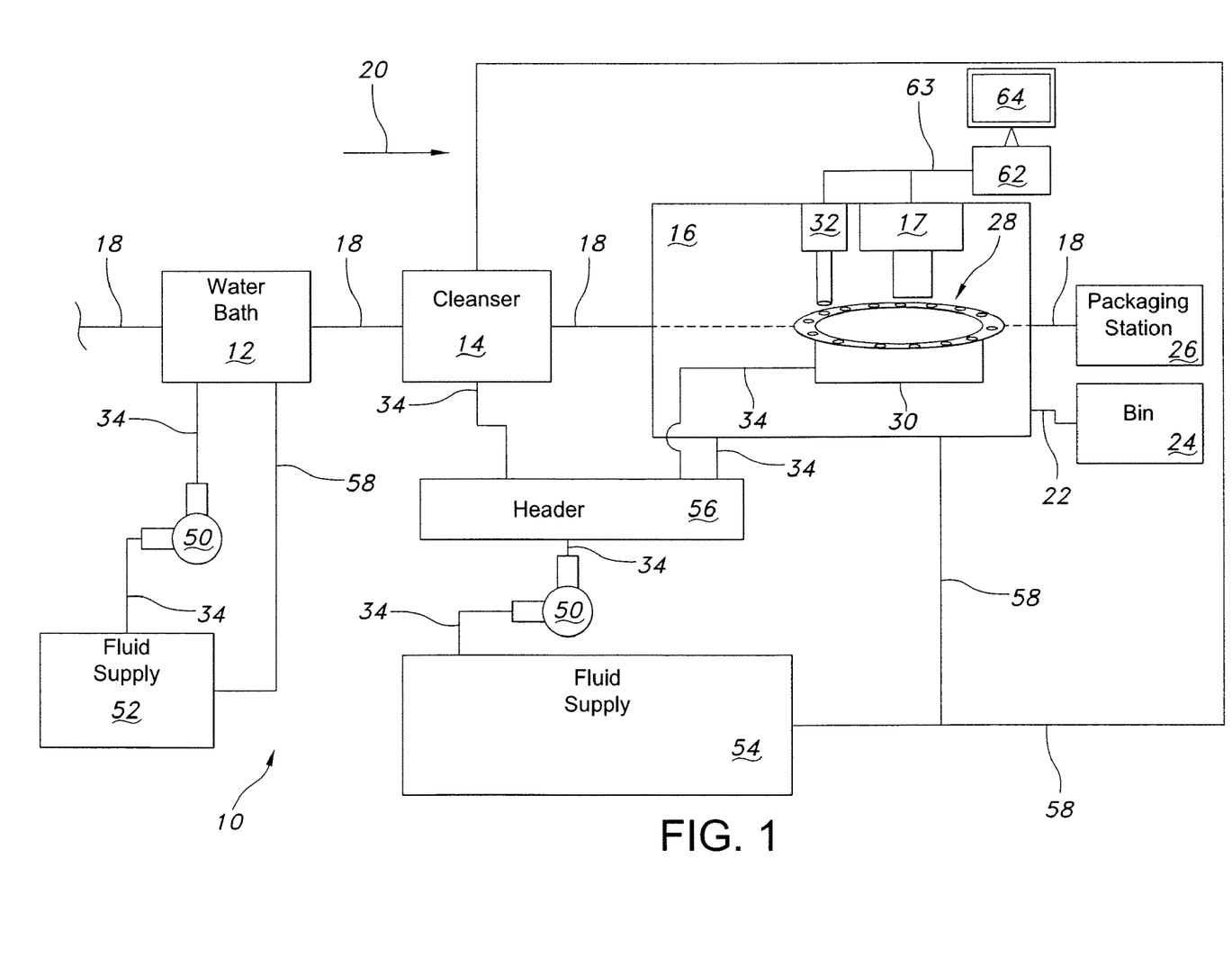
FIG. 1 is a partial diagrammatic illustration of an ophthalmic device forming system according to an exemplary embodiment of the present disclosure.

FIG. 1 illustrates an ophthalmic device forming system 10 according to an exemplary embodiment of the present disclosure. As shown in FIG. 1, the system 10 can include, for example, a water bath 12, a cleanser 14, an inspection station 16, and a packaging station 26. The water bath 12 can be connected to the cleanser 14 via a transport device 18 and the cleanser 14 can be connected to the inspection station 16 by the transport device 18. The packaging station 26 can also be connected to the inspection station 16 via the transport device 18. As shown in FIG. 1, the water bath 12 can be disposed upstream of the cleanser 14, the cleanser 14 can be disposed upstream of the inspection station 16, and the packaging station 26 can be disposed downstream of the inspection station 16. The system 10 can also include a vision system 28 and a vacuum device 32, and at least one of the vision system 28 and the vacuum device 32 can be connected to the inspection station 16. In an exemplary embodiment, the vision system 28 can include at least one sensor 17, and the vacuum device 32 can include an actuation assembly 36, a head 40, and a plurality of vacuum components 46.

In forming an ophthalmic device 70 (FIG. 2) such as, for example, a contact lens, casting molds can be dosed with a monomer, a polymer, and/or other lens forming materials. The entire casting mold assembly can then be placed into a curing apparatus where the ophthalmic device 70 can be formed and/or otherwise cured. Once the ophthalmic device 70 is formed, a posterior portion of the casting mold can be removed and discarded, and the formed ophthalmic device 70 can be substantially adhered to the remaining or anterior portion of the casting mold. The ophthalmic device 70 and the anterior portion of the casting mold can then be placed in, for example, an oven where residual solvents are driven out of the ophthalmic device 70 by heat and ventilation. A plunger mechanism can then be used to apply a pressure to a portion of the anterior portion of the casting mold and a lens handling device can be used to remove the separate lens. The anterior portion of the casting mold can then be discarded and the formed ophthalmic device 70 can be transported to an edge forming apparatus wherein at least a portion of the substantially circular edges of the ophthalmic device 70 are rounded. The ophthalmic device 70 can then be treated in a plasma environment and the treated ophthalmic device 70 can be transported to one or more machines configured to assist in removing impurities and inspecting the condition of the ophthalmic device 70.

In an exemplary embodiment, a treated ophthalmic device 70 can first be transported to the water bath 12 via the transport device 18. The transport device 18 can be any apparatus and/or collection of machines or devices useful in transporting items having optical quality surfaces from one machine to another machine in an assembly and/or manufacturing environment. The transport device 18 can include one or more gripping devices such as, for example, fingers, hooks, graspers, and/or any other gripping devices known in the art. Such gripping devices (not shown) can be configured to delicately grasp a fragile item such as, for example, a partially formed ophthalmic device and safely transport the fragile item from machine to machine without causing damage thereto. In an exemplary embodiment, the transport device 18 can also include one or more devices (not shown) configured to utilize suction and/or vacuum to handle and/or otherwise grasp the ophthalmic devices while not causing any damage to the one or more optical quality surfaces of the ophthalmic devices during transport.

In an additional exemplary embodiment of the present disclosure, the ophthalmic devices 70 formed and/or inspected by the system 10 can be housed in one or more carrying trays (not shown). The carrying trays can be transported from, for example, the water bath 12 to the cleanser 14 and then to the inspection station 16 by the transport device 18. In such an exemplary embodiment, the transport device 18 can be configured to transport the carrying trays between the components of the system 10 without causing any damage to, for example, the carrying trays and/or the ophthalmic devices 70 carried thereby. Alternatively, as discussed above, the transport device 18 can also be configured to transport ophthalmic devices 70 individually between the components of the system 10. In such an alternative exemplary embodiment, the carrying trays can be omitted.

With continued reference to FIG. 1, the water bath 12 can be any device known in the art configured to assist in fluidly removing debris, contaminants, and/or other foreign materials from an ophthalmic device such as, for example, a contact lens. Such foreign materials may be adhered to and/or otherwise carried with the ophthalmic device in an ophthalmic device forming process, and the foreign materials can be, for example, dirt, dust, and/or pieces of polymer or monomer material left over from upstream ophthalmic device forming and/or curing processes. In an exemplary embodiment, the water bath 12 can be configured to remove isopropyl alcohol from the ophthalmic devices transported thereto. Isopropyl alcohol can be carried with the ophthalmic devices from components of the system 10 disposed upstream of the water bath 12. The water bath 12 can be configured to receive ophthalmic devices 70 and/or other devices or carrying trays transported by the transport device 18.

The water bath 12 can include a housing and/or other components configured to receive and retain working fluid 42 such as, for example, water, isopropyl alcohol, saline solution and/or other cleansing or hydrating agents. The housing of the water bath 12 can be made from any metal and/or alloy known in the art such as, for example, FDA approved 316 stainless steel. The water bath 12 can be fluidly connected to a fluid supply 52 configured to store the working fluid 42 discussed above and/or direct a pressurized flow of the working fluid 42 to the water bath 12. The water bath 12 can also include one or more pressurization devices (not shown) configured to direct the working fluid 42 supplied from the fluid supply 52 towards the ophthalmic devices 70 delivered by the transportation device 18. In an exemplary embodiment, the pressurization devices can include one or more nozzles or other like structures.

The fluid supply 52 can be any drum, container, sump, or other fluid storage device known in the art configured to house and/or otherwise store a large volume of working fluid 42. In an exemplary embodiment, fluid supply 52 can be a fluid supply of the manufacturing facility in which the system 10 is operating. In such an exemplary embodiment, the fluid supply 52 can be a water tower or other like fluid storage device. As shown in FIG. 1, the fluid supply 52 can be fluidly connected to the water bath 12 via one or more supply lines 34. The supply lines 34 can be any tube, pipe, hose, and/or other structure known in the art configured to transmit a pressurized flow of fluid between two components in a production environment. The supply lines 34 can be made from any metal, alloy, plastic, and/or other material useful for transmitting pressurized flows of fluid, and such materials may include, PVC, copper, and FDA approved 316 stainless steel. In an exemplary embodiment, the supply lines 34 can be substantially rigid pipes. Alternatively, the supply lines 34 can be a combination of substantially rigid piping and substantially flexible hoses. The water bath 12 can also be fluidly connected to the supply 52 via a return line 58 configured to direct a flow of working fluid 42 from the water bath 12 to the fluid supply 52. The return line 58 can be mechanically similar to the supply lines 34 described above. In addition, it is understood that the fluid supply lines 34 and the return line 58 can include a number of valves and/or joints to assist in fluidly connecting the water bath 12 to the fluid supply 52.

A pump 50 can be fluidly connected between the fluid supply 52 and the water bath 12. The pump 50 can be configured to draw working fluid 42 from the fluid supply 12 and to supply a pressurized flow of the working fluid 42 to the water bath 12 via the supply lines 34. The pump 50 can be any fluid pressurization device known in the art such as, for example, a positive displacement pump or a rotodynamic pump. The pump 50 can also include a power source such as, for example, an electric motor configured to supply rotary power to, for example, an input shaft of the pump 50.

Referring again to FIG. 1, the cleanser 14 can be disposed adjacent to the water bath 12 and can be configured to receive ophthalmic devices 70 and/or other devices or carrying trays transported by the transport device 18. The cleanser 14 can include a housing and/or other components configured to contain fluids such as, for example, water. The cleanser 14 can be similar in construction to the water bath 12 and can be configured to cleanse and/or otherwise remove impurities from the ophthalmic devices 70 transported thereto. In an exemplary embodiment, the cleanser 14 can also include a cleansing agent supply and one or more pressurization devices (not shown). In an exemplary embodiment, the pressurization devices can include one or more nozzles or other like structures. The pressurization devices can be configured to inject and/or otherwise combine a mild soap-like cleaning agent or other cleaning agent with the working fluid 42 supplied from the fluid supply 52. A working fluid 42/cleaning agent mixture can, thus, be directed towards the ophthalmic devices 70 within a portion of the cleanser 14 to remove impurities from the devices 70.

As discussed above with respect to the water bath 12, the cleanser 14 can be fluidly connected to a fluid supply 54. The fluid supply 54 can be, for example, a tank, container and/or any other device configured to store and/or retain a supply of fluid such as, for example, water or other working fluids 42.

As shown in FIG. 1, a pump 50 can be configured to draw working fluid 42 from the fluid supply 54 and to supply a pressurized flow of working fluid 42 to the cleanser 14. In an exemplary embodiment, the pump 50 can be configured to direct a pressurized flow of working fluid 42 to a header 56. The header 56 can be, for example, a manifold or other device useful in delivering a pressurized flow of fluid to a plurality of components. The cleanser 14, header 56, and/or fluid supply 54 can be made from any of the materials discussed above with respect to the supply line 34 and return line 58. In an exemplary embodiment, the cleanser 14, header 56, and/or fluid supply 54 can be made from FDA approved 316 stainless steel or other like metals or alloys. The pump 50 connecting the fluid supply 54 to the header 56 can be substantially similar to the pump 50 connecting the fluid supply 52 to the water bath 12. In an additional exemplary embodiment, the pump 50 fluidly connected to the fluid supply 54 can have a greater pumping capacity than the pump 50 fluidly connected to the fluid supply 52. As shown in FIG. 1, working fluid 42 from the fluid supply 54 can be directed to the cleanser 14 via supply lines 34 and working fluid 42 exiting in the cleanser 14 can be returned to the fluid supply 54 via the return line 58.

The inspection station 16 can be disposed adjacent to the cleanser 14, and cleaned ophthalmic devices 70, carrying trays, and/or other ophthalmic device handling components can be transported from the cleanser 14 to the inspection station 16 by the transport device 18. The inspection station 16 can be any conventional ophthalmic device inspection station or other like apparatus known in the art. The inspection station 16 can include, for example, a housing similar to the housings described above with respect to the water bath 12 and the cleanser 14. The inspection station 16 can be configured to receive a pressurized flow of working fluid 42 from the fluid supply 54. As shown in FIG. 1, a supply line 34 can be configured to direct a pressurized flow of the working fluid 42 from the header 56 to the inspection station 16. It is understood that, in an exemplary embodiment, the inspection station 16 and/or the cleanser 14 can be connected to dedicated pumps 50. In such an exemplary embodiment, the header 56 can be removed, and the cleanser 14 and/or the inspection station 16 and their corresponding pumps 50 can be connected directly to the fluid supply 54.

As shown in FIG. 1, a carousel 30 can be mounted within and/or otherwise connected to the inspection station 16. The carousel 30 can be any known assembly and/or collection of components configured to receive a plurality of ophthalmic devices 70 and maintain the ophthalmic devices 70 in a hydrated state during inspection by one or more sensors 17. In an exemplary embodiment, the vision system 28 can be a computerized vision system, and the carousel 30 can be a component of the vision system 28 configured to retain, submerge, and/or otherwise hydrate a plurality of ophthalmic devices 70 within a volume of working fluid 42 during inspection by the sensor 17.

Figure 2:
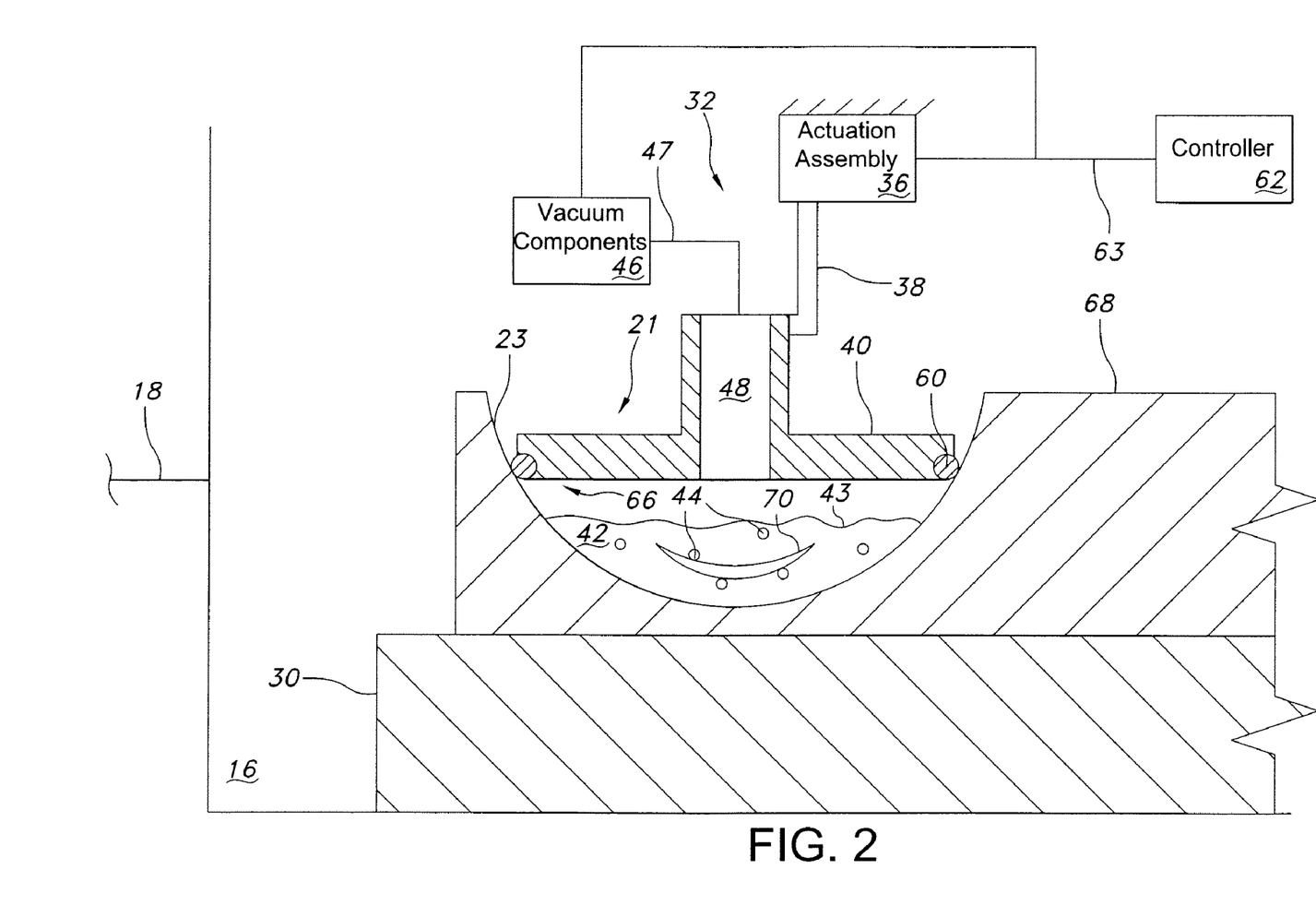
FIG. 2 is a partial diagrammatic illustration of a portion of the system shown in FIG. 1.

The carousel 30 can be any shape, size, and/or other configuration known in the art, and can have a number of moving components configured to assist in positioning the ophthalmic devices 70 requiring inspection proximate one or more components of the inspection station 16 such as, for example, the sensor 17. In an exemplary embodiment, the carousel 30 can include a receptacle 68 (FIG. 2) configured to assist in immobilizing and/or otherwise retaining individual ophthalmic devices 70 during the inspection process. The receptacle 68 can be, for example, movably mounted to the carousel 30 such that the ophthalmic devices 70 disposed thereon can be desirably positioned proximate the sensor 17 during inspection. The receptacle 68 can define a plurality of inspection cells 21, and each inspection cell 21 can be configured to receive and retain a volume of working fluid 42. The inspection cells 21 can be sized, shaped, and/or otherwise configured to retain and/or immobilize an ophthalmic device 70 during the inspection process. As shown in FIG. 2, the receptacle 68 can define a wall 23 of the inspection cells 21 and the inspection cells 21 can be substantially concave in shape.

As shown in FIG. 1, the carousel 30 can be fluidly connected to, for example, the header 56 and the fluid supply 54 by supply line 34. Thus, the carousel 30 and in particular, the inspection cells 21, can be configured to maintain the ophthalmic devices 70 disposed therein in a substantially submerged state during inspection by the sensor 17. It is understood that the fluids used to submerge the ophthalmic devices 70 can be, for example, working fluids 42 such as de-ionized water and/or other like aqueous liquids stored within the fluid supply 54.

Although not shown in FIGS. 1 and 2, it is understood that the system 10 can also include a handling device disposed proximate, for example, the carousel 30. The handling device can be any apparatus and/or collection of machines or devices useful in safely transporting items having optical quality surfaces from one location within a machine to another location within the same machine in an assembly and/or manufacturing environment. The handling device can include, for example, a probe, a suction device, and/or one or more gripping devices configured to assist in safely transporting and/or otherwise handling an ophthalmic device 70. The handling device can be configured to delicately grasp and/or handle, for example, an ophthalmic device 70 and safely transport the ophthalmic device 70 from a first position within a component of the system 10 to a second position within the component of the system 10 without causing damage to the ophthalmic device 70. For example, the handling device can be configured to remove an ophthalmic device 70 from the transport device 18 and place the removed ophthalmic device 70 within the inspection cell 21 of the carousel 30 without causing damage to the optical surfaces of the ophthalmic device 70.

As shown in FIGS. 1 and 2, the vacuum device 32 can be disposed proximate and/or at least partially connected to the inspection station 16. The vacuum device 32 can be configured to assist in removing gases entrained within working fluid 42 disposed within the inspection cells 21 of the carousel 30. In particular, the vacuum device 32 can be configured to assist in removing bubbles 44 that are entrained in the working fluid 42 disposed within each inspection cell 21. The vacuum device 32 can also be configured to assist in removing bubbles 44 that are adhered to ophthalmic devices 70 disposed in each inspection cell 21 and substantially submerged in the working fluid 42. The vacuum device 32 can assist in removing such bubbles 44 by directing a negative pressure to and/or otherwise reducing the pressure of the working fluid 42 disposed within the inspection cell 21. It is understood that such a reduction in pressure can cause a portion of the working fluid 42 to boil. It is also understood that directing a negative pressure to the working fluid 42 can include substantially directing a vacuum thereto.

As discussed above, in an exemplary embodiment, the vacuum device 32 can include an actuation assembly 36, a head 40, and a plurality of vacuum components 46. The head 40 can comprise any nozzle, fitting, tool, or other air handling device known in the art configured to deliver a localized negative pressure (i.e., pressure reduction) to a portion of a machine in a manufacturing and/or assembly environment. The head 40 can be any shape, size, and/or other configuration known in the art and, in an exemplary embodiment, the head 40 can be configured to assist in forming a substantially air-tight and/or fluid-tight seal with an inspection cell 21 of the carousel 30. As shown in FIG. 2, the head 40 can be sized and/or shaped such that a portion of the head 40 can fit substantially within an inspection cell 21 while forming this seal. Alternatively, a perimeter of the head 40 can be larger than an opening of the inspection cell 21. In such an exemplary embodiment, the head 40 can be sized and/or shaped to sit substantially on top of and/or outside of the inspection cell 21 while engaging the inspection cell 21 and forming the seal. The head 40 can be made from, for example, any common metals, plastics, alloys, polymers, or other materials capable of assisting in delivering a negative pressure. Such materials can include, for example, aluminum, stainless steel, PVC, and/or any other materials known in the art.

The head 40 can define one or more channels 48 configured to assist in delivering a negative pressure to the inspection cell 21 and its contents. The channel 48 can be sized and/or shaped to assist in delivering the negative pressure to the inspection cell 21 substantially uniformly, and it is understood that the channel 48 can be sized and/or shaped to deliver a desirable level of negative pressure and/or vacuum to the inspection cell 21. For example, a first ophthalmic device inspection application may require delivering approximately 10 Torr of negative pressure to the inspection cell 21 and a second ophthalmic device inspection application may require delivering approximately 20 Torr of negative pressure to the inspection cell 21. In such an example, the first application may require a smaller head 40 and/or a smaller diameter channel 48 than the second application. It is understood that the effective removal of bubbles 44 from the working fluid 42 can occur when negative pressures of approximately 10 Torr and greater are delivered to the inspection cell 21 and its components.

The head 40 can also include any structure or device capable of assisting in forming a substantially fluid-tight seal between the head 40 and the inspection cell 21. As shown in FIG. 2, such structures may include any number of o-rings, gaskets, stops, or other structures known in the art. In an exemplary embodiment, a gasket 60 can be fixedly attached to the head 40 and can be sized, shaped, and/or otherwise configured to mate with the wall 23 of the inspection cell 21 to assist in forming the substantially fluid-tight seal discussed above. In an alternative exemplary embodiment in which the head 40 is sized to sit substantially on top or and/or outside of the inspection cell 21 while engaging the inspection cell 21, the gasket 60 can be sized, shaped, and/or otherwise configured to mate with a portion of the receptacle 68 such as, for example, a top surface of the receptacle 68. The gasket 60 can be made from any material useful in forming a substantially fluid-tight seal with a substantially metal machine component in an assembly and/or manufacturing environment, and such materials can include, for example, any plastic, rubber, polymer, or foam known in the art.

As illustrated in FIG. 2, once the head 40 has been positioned with respect to the inspection cell 21 to form the substantially fluid-tight seal, the head 40 and the inspection cell 21 can define a sealed region 66 above and/or proximate a surface 43 of the working fluid 42 disposed in the inspection cell 21. The sealed region 66 can contain a pocket of ambient air, and the ambient air within the sealed region 66 can be evacuated, exhausted, and/or otherwise substantially removed from the inspection cell 21 upon delivering a negative pressure thereto. In an exemplary embodiment, the trapped ambient air can be substantially removed and/or otherwise evacuated from the sealed region 66 via the channel 48 once the substantially fluid-tight seal has been formed and a desired negative pressure has been applied to the inspection cell 21 and/or the working fluid 42 disposed therein. As will be discussed below, the vacuum components 46 of the vacuum device 32 can be pneumatically and/or otherwise fluidly connected to the channel 48 and can be configured to assist in delivering the desired negative pressure to the inspection cell 21.

Components of the vacuum device 32 such as, for example, the head 40, can be controllably and/or otherwise programmably movable relative to the carousel 30, the inspection cells 21, and/or the ophthalmic devices 70 disposed therein. Such relative movement can be facilitated by the actuation assembly 36. The actuation assembly 36 can include, for example, tracks, motors, belts, and/or other devices (not shown) configured to enable relative movement between the components of the vacuum device 32 and, for example, the inspection cells 21. As shown in FIG. 2, the actuation assembly 36 can include, for example, a robotic and/or otherwise mechanized arm 38 configured to controllably position the head 40 proximate the inspection cells 21.

The arm 38 can be mounted to, for example, a mechanized belt or other structure such that the head 40 can have a full range of motion relative to the carousel 30 in both the horizontal and vertical planes. For example, the arm 38 may be configured to move the head 40 in any direction or position laterally (in a horizontal plane) until the head 40 is desirably positioned directly over one of the inspection cells 21. Once the head 40 has been properly laterally positioned, the arm 38 may be configured to lower (in a vertical plane) the head 40 on top of or at least partially into the inspection cell 21 until the gasket 60 contacts the wall 23 of the inspection cell 21. Thus, the arm 38 can assist the head 40 in forming the sealed region 66 discussed above. Components of the actuation assembly 36 can also be electrically connected to, for example, a controller 62 (described in further detail below) configured to assist in controlling the position, movement, activation, and/or deactivation thereof. Such a connection is shown by the connection line 63 in FIG. 2.

In an exemplary embodiment of the present disclosure, the vacuum components 46 of the vacuum device 32 can be configured to assist in delivering a desired amount of negative pressure to a portion of the inspection cell 21 and/or the working fluid 42 disposed therein. The vacuum components 46 can include, for example, one or more electric motors, pumps, compressors, filters, and/or other vacuum equipment known in the art. As shown in FIG. 2, the vacuum components 46 can be pneumatically and/or otherwise fluidly connected to the head 40 via a vacuum line 47. The vacuum line 47 can be any tube, pipe, hose, or other known structure configured to transmit fluids at a negative pressure between two components. The vacuum line 47 may be, for example, fluidly connected to the channel 48 of the head 40 and may be substantially flexible so as to maintain a fluid connection between the channel 48 and the vacuum components 46 while the position of the head 40 is adjusted within the inspection station 16. A wall strength of the vacuum line 47 may be such that the vacuum line 47 is capable of transmitting fluids at any desirable amount of negative pressure without substantially deforming and/or caving the vacuum line 47.

The vacuum components 46 can be controlled to produce a constant negative pressure or a variable negative pressure, and the vacuum components 46 can be controlled to desirably produce any range of negative pressure (i.e., vacuum) based on the amount of pressure needed for a particular ophthalmic device inspection application. For example, in a first application, the vacuum components 46 may be controlled to produce and/or otherwise direct approximately 10 Torr of negative pressure to the inspection cell 21 once the substantially fluid-tight seal has been formed, and in a second application, the vacuum components 46 may be controlled to produce and/or otherwise direct approximately 20 Torr of negative pressure to the inspection cell 21. One or more of the vacuum components 46 can be electrically connected to, for example, the controller 62, and the controller 62 can assist in controlling the activation, deactivation, and amount of negative pressure produced thereby. Such a connection is shown by the connection line 63 in FIG. 2.

In delivering such negative pressures, the vacuum components 46 of the vacuum device 32 can assist in creating a pressure difference between the working fluid 42 and the entrained gases forming bubbles 44 therein. In particular, substantially delivering a vacuum to the sealed region 66 can cause a dimension, volume, surface area, and/or other quantifiable aspect of the bubbles 44 such as, for example, a diameter thereof, to increase. It is understood that when the pressure within the sealed region 66 is reduced, the bubbles 44 will begin to expand. Expansion of the bubbles 44 may increase the buoyancy of the bubbles 44, which may cause the bubbles 44 to rise to the surface 43 of the working fluid 42. The expansion of the bubbles 44 may also cause the bubbles 44 to burst. In addition, when the pressure within the sealed region 66 is reduced below the vapor pressure of the working fluid 42 disposed in the inspection cell 21, at least a portion of the working fluid 42 may begin to boil. Boiling at least a portion of the working fluid 42 can assist in mechanically agitating the working fluid 42, and such agitation can assist in freeing bubbles 44 adhered to the ophthalmic device 70 or entrained in the working fluid 42.

The gases released from the bursted bubbles 44 can pass through, for example, the sealed region 66 and the channel 48, and can be exhausted to the atmosphere via one or more of the vacuum components 46. Alternatively, the released gases can collect within the inspection station 16 and can be vented to atmosphere or to the manufacturing facility in which the system 10 is operating. The released gases can include any gases commonly found in the earth's atmosphere such as, for example, oxygen, carbon dioxide, and air. In addition, as discussed above, the working fluid 42 can be any fluid known in the art such as, for example, de-ionized water, isopropyl alcohol, saline solution, and/or any other hydrating and/or cleansing agent.

Figure 3:
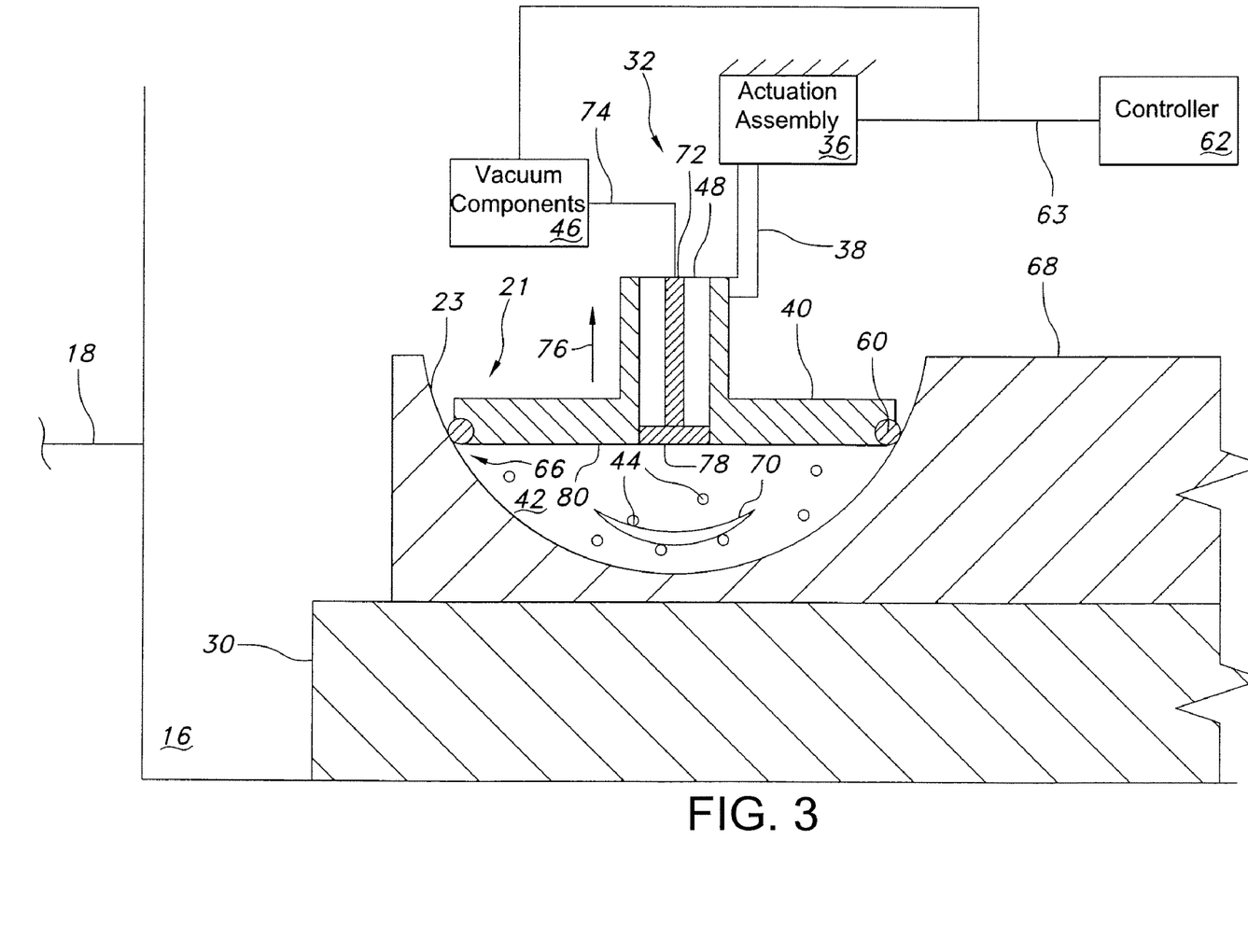
FIG. 3 is a partial diagrammatic illustration of a portion of the system shown in FIG. 1 according to an additional exemplary embodiment of the present disclosure.

As shown in FIG. 3, in an additional exemplary embodiment of the present disclosure, the vacuum components 46 of the vacuum device 32 can include a piston 72 and an arm 74. In such an embodiment, the vacuum line 47 can be omitted. The piston 72 can be sized, shaped, and/or otherwise configured to be received by the channel 48 of the head 40. The piston 72 can be made from, for example, any of the materials discussed above with respect to the head 40, and the piston 72 can be movably mounted within the channel 48. The piston 72 can include, for example, one or more o-rings, gaskets, stops, or other sealing structures (not shown) known in the art. In an exemplary embodiment, such sealing structures can be fixedly attached to the piston 72, and can be sized, shaped, and/or otherwise configured to mate with the channel 48 such that a substantially fluid-tight seal can be maintained between the piston 72 and the head 40 when the piston 72 is moved within the channel 48.

In an exemplary embodiment, the piston 76 can be moved between an extended position (shown in FIG. 3) and a retracted position, at least partially, within the head 40. When in the extended position, an undersurface 78 of the piston 72 can be substantially co-planar with an undersurface 80 of the head 40. It is understood that the head 40 can be disposed within the inspection cell 21 such that the working fluid 42 can contact the undersurface 80. As shown in FIG. 3, when the head 40 is so positioned, and when the piston 72 is in the extended position, substantially no ambient air may be trapped between the head 40 and the working fluid 42. Alternatively, the head 40 and the piston 72 can be positioned relative to the working fluid 42 to trap a volume of ambient air proximate the surface 43 (FIG. 2) of the working fluid 42. As shown in FIG. 3, when the substantially fluid-tight seal is formed, the head 40 and a portion of the piston 72 can assist in defining the sealed region 66.

The piston 72 can be retracted and/or otherwise moved in the direction of arrow 76 to achieve an increase in the enclosed volume of the sealed region 66. For example, once the head 40 has been positioned, as shown in FIG. 3, to form a substantially fluid-tight seal with the inspection cell 21, moving the piston 72 in the direction of arrow 76 can increase the volume of the sealed region 66 and can assist in directing a negative pressure to the working fluid 42 and/or ophthalmic devices 70 or other objects disposed within the inspection cell 21 for inspection. In particular, retracting the piston 72, after the substantially fluid-tight seal has been formed, can expose the working fluid 42 in the inspection cell 21 to a larger volume without exposing the working fluid 42 to any additional ambient air. Thus, directing a negative pressure to the working fluid 42 with the components illustrated in FIG. 3 can assist in removing bubbles 44 entrained within the working fluid 42 and can have substantially the same effects as discussed with regard to the exemplary embodiment of the system 10 illustrated in FIG. 2.

The piston 72 can be transitioned between the extended position and the retracted position, retracted in the direction of arrow 76, and/or otherwise actuated by the arm 74 connected thereto. The arm 74 can comprise, for example, any known robotic, mechanized, electromechanical, pneumatic, and/or other components configured to controllably position a piston within a channel, cylinder, or other confined space. The arm 74 can be substantially similar to the arm 38 discussed above with respect to the actuation assembly 36, and the arm 74 and other vacuum components 46 can be controllably connected to the controller 62. It is understood that once a substantially fluid-tight seal has been formed, the amount of negative pressure delivered to the sealed region 66 can be defined by and/or be directly related to the position and/or displacement of the piston 72 within the channel 48.

Referring again to FIG. 1, the sensor 17 associated with the inspection station 16 can be any diagnostic device such as, for example, a thermocouple, a camera, and/or a pressure sensor, configured to sense one or more characteristics of an ophthalmic device 70. In an exemplary embodiment, the sensor 17 can be a high resolution camera and/or other video, photographic, or imaging device configured to sense, measure, and/or otherwise analyze an ophthalmic device 70 delivered in proximity thereto. It is understood that a human operator can also perform the functions of the sensor 17 and in such an embodiment, removing bubbles 44 utilizing the systems and methods discussed herein can assist in reducing the number of false rejects made by a human operator during an inspection process. In such an exemplary embodiment, it may be possible to omit the sensor 17. As discussed above, the inspection cell 21 and/or other components of the inspection station 16 can be configured to retain ophthalmic devices 70 substantially submerged in a volume of working fluid during inspection. Accordingly, the sensor 17 can be configured to obtain images of the ophthalmic devices 70 in a substantially aqueous environment.

The sensor 17 can be configured and/or otherwise mounted within the inspection station 16 to be controllably and/or programmably movable relative to the carousel 30 and/or the ophthalmic devices 70 disposed therein. The sensor 17 can be mounted to tracks, motors, belts, robot arms, and/or other devices (not shown) configured to enable relative movement between the sensor 17 and ophthalmic devices 70 delivered to the inspection station 16.

The sensor 17 can be electrically connected to the controller 62 of the system 10. The controller 62 can include, for example, an ECU, a computer, and/or any other electrical control device known in the art. The controller 78 can include one or more operator interfaces 64 such as, for example, a monitor, a keyboard, a mouse, a touch screen, and/or any other devices useful in entering, reading, storing, and/or extracting data from the devices to which the controller 62 is connected. The controller 62 can be configured to exercise one or more control algorithms and/or control the devices to which it is connected based on one or more preset programs. For example, the controller 62 can be configured to control the sensor 17 to obtain images of ophthalmic devices 70 delivered to the inspection station 16. The controller 62 can also be configured to operate and/or otherwise execute image software loaded thereon and configured to inspect the images obtained by the sensor for defects in the ophthalmic devices 70. The controller 62 can also be configured to store and/or collect images and/or other data regarding the ophthalmic devices 70 that are observed. Such data can assist a user in determining the quality and/or usability of the observed ophthalmic device 70.

The controller 62 can be connected to, for example, the sensor 17 and/or a component of the ultrasonic degassing assembly 74 via one or more connection lines 63. The pumps 50, the motors (not shown) connected to pumps 50, and/or other devices of the system 10 can also be electrically connected to the controller 62 via connection lines 63 (not shown). The connection lines 63 can consist of any conventional electrical connection means known in the art such as, for example, wires or other like connection structures, as well as wireless communication means. Through these electrical connections, the controller 62 can be configured to receive, for example, sensed image data from the sensor 17. In particular, the controller 62 can be configured to receive images of the optical quality surfaces of the ophthalmic devices 70 delivered to the inspection station 16. Based on the sensed images, the controller 62 can be configured to control the system 10 to accept the inspected ophthalmic for commercial sale or reject the ophthalmic devices 70 based on one or more detected impurities, lens deformations, and/or other ophthalmic device characteristics.

The transport device 18 can be configured to direct accepted ophthalmic devices 70 from the inspection station 16 to the packaging station 26 of the system 10. The packaging station 26 can be disposed downstream of the inspection station 16 and can be configured to package the accepted ophthalmic devices 70 into, for example, a blister package useful for commercial sale. The inspection station 16 can also be configured to direct the rejected ophthalmic devices 70 to a bin 24 via a transport device 22. The transport device 22 can be substantially similar in configuration to the transport device 18 and the bin 24 can be, for example, a reject bin of the system 10. Ophthalmic devices 70 directed to the bin 24 can be melted down and/or otherwise recycled for use in future ophthalmic device forming processes. Alternatively, the ophthalmic devices 70 directed to bin 24 can be discarded.

INDUSTRIAL APPLICABILITY

The ophthalmic device forming system 10 of the present disclosure can be used with a series of other machines for the inspection and/or formation of ophthalmic devices 70 such as, for example, contact lenses. The system 10 can be configured for use with and/or otherwise included in, for example, an assembly line used to manufacture contact lenses and, in an exemplary embodiment, the system 10 can be used to inspect one or more ophthalmic devices 70 prior to packaging the devices 70 in a blister pack or other commercial sale container. Removing any large bubbles disposed upon, adhered to, and/or otherwise carried by one or more surfaces of the ophthalmic devices 70 can have many advantages including, for example, making it easier to place the devices 70 in the sales container since the devices 70 will be less likely to float when dispersed a solution. Removing bubbles from the ophthalmic devices 70 and/or the working fluid 42 prior to inspection can also increase the accuracy with which defects are detected by components of the system 10 such as, for example, the sensor 17. Although described above with respect to the formation of ophthalmic devices 70, it is understood that aspects of the exemplary system 10 and methods of the present disclosure could also be used in other aqueous inspection environments such as, for example, the manufacture of other medical devices and food. In still further exemplary embodiments, aspects of the system 10 and methods of the present disclosure could be used in manual inspection processes.

It is understood that, due to the turbulent flow of the working fluid 42, gases such as, for example, air can become entrained within the working fluid 42 delivered to, for example, the water bath 12, the cleanser 14, and/or the inspection station 16. Once entrained within the working fluid 42 these gases form the bubbles 44 illustrated in FIG. 2. At least some of the entrained bubbles 44 carried by the working fluid 42 can adhere to one or more surfaces of the ophthalmic devices 70 and can remain adhered to the ophthalmic devices 70 as the ophthalmic devices 70 are transported to the inspection station 16. Detection of the entrained and/or adhered bubbles 44 by the sensor 17 can result in the indication of a false negative on an otherwise acceptable ophthalmic device 70. Substantially eliminating the bubbles 44 using the vacuum device 32 discussed above, however, can substantially reduce the number of false negatives indicated by the system 10 and can thereby increase the efficiency and overall throughput thereof.

In an exemplary ophthalmic device inspection and/or forming process of the present disclosure, the transport device 18 can deliver one or more ophthalmic devices 70 to the water bath 12. Upon receiving the ophthalmic devices 70, the pump 50 can be activated to supply a pressurized flow of working fluid 42 from the fluid supply 52, through supply line 34, to the water bath 12. The water bath 12 can substantially immerse and/or otherwise wash the ophthalmic devices 70 therein with the pressurized flow of working fluid 42 such that substantially all impurities and/or other foreign objects are removed from the optical quality surfaces of the ophthalmic devices 70. In addition, the water bath 12 can assist in removing isopropyl alcohol carried by the ophthalmic devices 70. A portion of the working fluid 42 supplied to the water bath 12 can return to the fluid supply 52 via the return line 58.

As illustrated by arrow 20 in FIG. 1, the ophthalmic devices 70 can then be transferred from the water bath 12 to the cleanser 14 via the transport device 18. The pump 50 can supply a pressurized flow of the working fluid 42 to the header 56 and the supply lines 34 can direct the pressurized flow to the cleanser 14. In addition, components of the cleanser 14 can direct a mild soap-like agent and/or other like lens cleaning agents to the ophthalmic devices 70. In an exemplary embodiment, the lens cleaning agents can be mixed with the pressurized flow of working fluid 42 delivered to the cleanser 14. Once the pressurized flow of working fluid 42 has been supplied to the cleanser 14, a portion of the working fluid 42 can be returned to the fluid supply 54 via the return line 58.

After the ophthalmic devices 70 have been acted upon by the cleanser 14, the ophthalmic devices 70 can then be transferred to the inspection station 16. The ophthalmic devices 70 can again be substantially submerged in a volume of working fluid 42 within the inspection station 16 so as not to dehydrate the ophthalmic devices 70 during inspection. For example, each of the ophthalmic devices 70 can disposed within an inspection cell 21 of the carousel 30, and can be substantially submerged in working fluid 42 disposed therein. Once submerged, a plurality of bubbles 44 can adhere to one or more surfaces of the ophthalmic devices 70 and can also remain entrained within the working fluid 42.

To assist in removing the bubbles 44 from one of the inspection cells 21, the head 40 of the vacuum device 32 can be manipulated and/or otherwise positioned with respect to the inspection cell 21 to form a substantially fluid-tight seal between the inspection cell 21 and the head 40. Once this seal is formed, a sealed region 66 may be defined proximate the surface 43 of the working fluid 42, and a pocket of ambient air may be trapped within the sealed region 66.

In forming the seal discussed above, the arm and/or other components of the actuation assembly 36 may be manipulated and/or otherwise controlled such that the gasket 60 connected to the head 40 may engage the wall 23 of the inspection cell 21. The head 40 can be positioned relative to the inspection cell 21 either manually or under the direction of one or more position control algorithms executed by the controller 62. For example, the head 40 can be automatically repositioned with respect to each of the inspection cells 21 of the carousel 30. The receptacle 68 and/or the inspection cells 21 can also be configured to automatically rotate and/or otherwise assist in positioning the ophthalmic devices 70 relative to the head 40.

Once the head 40 has been properly positioned and the seal formed, one or more of the vacuum components 46 can be activated to produce a desired negative pressure (i.e., a vacuum). The vacuum components 46 and the head 40 of the vacuum device 32 can then direct the negative pressure to the inspection cell 21 and its components. In an exemplary embodiment, the desired negative pressure can be at least 10 Torr. The negative pressure directed to the working fluid 42 can create a pressure difference between the working fluid 42 and the gases within the bubbles 42, and this pressure difference can cause a diameter of the bubbles 44 to increase. Eventually, the bubbles 44 will burst and the gases released can escape the working fluid 42.

In particular, the negative pressure can substantially remove the air pocket trapped within the sealed region 66 via the channel 48 and the vacuum line 47, thereby creating conditions approximating a vacuum in the sealed region 66.

As the pressure within the sealed region 66 drops below an ambient pressure of the inspection station 16, the bubbles 44 within the working fluid 42 can expand, rise to the surface 43, and burst. The gases released when the bubbles 44 burst can be removed from the sealed region 66 via the channel 48 and the vacuum line 47. In addition, when the pressure within the sealed region 66 drops below a vapor pressure of the working fluid 42, a portion of the working fluid 42 can start to boil, thereby providing mechanical agitation to the working fluid 42 and further assisting in the removal of bubbles 44 from the working fluid 42.

It is understood that the components illustrated in FIG. 3 can also be used to remove the bubbles 44 from the working fluid 42 in substantially the same way. For example, once the head 40 has been properly positioned and the substantially fluid-tight seal formed, the piston 72 can be displaced in the direction of arrow 76 and/or transitioned from the extended position shown in FIG. 3 to a retracted position. The arm 74 can be controlled to move the piston 72 in the direction of arrow 76 to achieve the retracted position. Actuating the piston 72 in this way can increase the volume of the sealed region 66, thereby directing a desired negative pressure (i.e., a vacuum) to the working fluid 42 within the inspection cell 21. As the pressure within the sealed region 66 drops below an ambient pressure of the inspection station 16, the bubbles 44 within the working fluid 42 can expand and burst. As discussed above, when the pressure within the sealed region 66 drops below a vapor pressure of the working fluid 42, a portion of the working fluid 42 can start to boil, further assisting in the removal of bubbles 44 from the working fluid 42. The gases released when the bubbles 44 burst can collect within the channel 48 proximate the underside 78 of the piston 72. The collected gases can be released to, for example, the inspection cell 16 once the seal between the head 40 and the receptacle 68 is broken.

Referring again to FIG. 2, once substantially all of the bubbles 42 have been removed from the surfaces of the ophthalmic device 70 and/or from the working fluid 42, the vacuum components 46 can be deactivated and a volume of ambient air may be allowed to reenter the sealed region 66 through, for example, the channel 48. Once a sufficient volume of air has entered the sealed region 66, the seal formed by the gasket 60 may be broken and the head 40 may be removed from its position proximate the inspection cell 21. Breaking the seal formed by the gasket 60 and/or removing the head 40 can cause the pressure of the working fluid 42 to increase to approximately the ambient pressure of the inspection station 16.

With the working fluid 42 and the ophthalmic device 70 free from bubbles 44, the sensor 17 can be manipulated and/or otherwise positioned to sense and/or otherwise detect a characteristic of the ophthalmic devices 70. As discussed above, such a characteristic can include, for example, surface quality, diameter, and/or other detectable characteristics. Such a characteristic could also include, for example, any trademarks, symbols, logos, characters, or other product/source identifiers. The sensor 17 can obtain one or more images of the ophthalmic devices 70 being examined and can transmit the obtained images to the controller 62 whereby the controller 62 may, through the use of preloaded examination software, determine the status, health, and/or quality of the ophthalmic device being examined. In particular, the software executed by the controller 62 can determine whether or not the examined ophthalmic device contains any defects. Based on this defect determination, the controller 62 can determine whether to allow the ophthalmic device 70 to be passed on from the inspection station 16 to the packaging station 26 for insertion and/or packaging within a blister pack or other commercial sale container. Alternatively, if the detected characteristic is not satisfactory, the controller 62 can make the determination to reject the examined ophthalmic device 70 and pass the rejected device 70 to the bin 24 via the transport device 22.

Other embodiments of the disclosed system 10 will be apparent to those skilled in the art from consideration of this specification. It is intended that the specification and examples be considered as exemplary only, with the true scope of the invention being indicated by the following claims.

What is claimed is:

1. A bubble removal system, comprising:
an inspection cell configured to receive an ophthalmic device and a volume of working fluid; and
a vacuum device configured to form a substantially fluid-tight seal with the inspection cell and to direct a negative pressure to the volume of working fluid and the ophthalmic device within the inspection cell, wherein the vacuum device comprises a head defining at least one channel, a piston and an arm, a portion of the piston being disposed within the at least one channel.

2. The system of claim 1, wherein a component of the vacuum device is controllably moveable relative to the inspection cell to assist in forming the substantially fluid-tight seal.

3. The system of claim 1, wherein the inspection cell is a component of an inspection station disposed upstream of a packaging station.

4. The system of claim 1, wherein the vacuum device is configured to assist in removing at least one bubble defined by the working fluid.

5. The system of claim 1, wherein the vacuum device is configured to assist in bringing a portion of the working fluid to a boil.

6. The system of claim 1, wherein the vacuum device is configured to assist in defining a sealed region of the inspection cell, the sealed region containing ambient air disposed adjacent to a surface of the working fluid.

7. The system of claim 6, wherein the vacuum device is configured to assist in substantially evacuating the ambient air from the sealed region.

8. The system of claim 6, wherein the vacuum device is configured to reduce a pressure of the sealed region below a vapor pressure of the working fluid.

9. The system of claim 1, wherein the head is connected to an actuation assembly configured to control the position of the head relative to the inspection cell.

10. The system of claim 1, wherein the vacuum device further comprises a vacuum line and a compressor, the vacuum line being fluidly connected to the at least one channel.

11. The system of claim 1, wherein the portion of the piston forms a substantially fluid-tight seal with the at least one channel.

12. A method of removing bubbles formed in a volume of working fluid, comprising:
disposing an ophthalmic device within the volume of working fluid, the volume of working fluid being contained within an inspection cell;
forming a sealed region between the inspection cell and a vacuum device;
directing a negative pressure to the sealed region with the vacuum device which includes increasing a volume of the sealed region; and
removing at least one bubble from the volume of working fluid.

13. The method of claim 12, wherein the at least one bubble is adhered to the ophthalmic device.

14. The method of claim 12, wherein directing the negative pressure to the sealed region includes bringing a portion of the working fluid to a boil.

15. The method of claim 12, further including trapping ambient air in the sealed region and substantially evacuating the ambient air from the sealed region.

16. The method of claim 12, wherein directing the negative pressure to the sealed region includes increasing a dimension of the at least one bubble.

17. The method of claim 12, wherein increasing the volume of the sealed region includes transitioning a piston of the vacuum device from an extended position to a retracted position, the piston forming a portion of the sealed region.

18. A method of preparing a volume of working fluid for the inspection of an ophthalmic device, comprising:
substantially submerging the ophthalmic device in the working fluid;
reducing a pressure of the working fluid below an ambient pressure;
bringing a portion of the working fluid to a boil;
increasing the pressure of the working fluid to the ambient pressure; and
sensing at least one characteristic of the ophthalmic device while the ophthalmic device is substantially submerged in the working fluid.

19. The method of claim 18, further including defining a sealed region, the sealed region containing the working fluid and a pocket of ambient air disposed adjacent to a surface of the working fluid.

20. The method of claim 18, further including packaging the ophthalmic device based on the sensing of the at least one characteristic.

21. The method of claim 18, further including removing at least one bubble from the working fluid.

22. The method of claim 18, wherein reducing the pressure of the working fluid includes defining a sealed region containing the working fluid and increasing a volume of the sealed region.

23. The method of claim 22, wherein increasing the volume of the sealed region includes transitioning a piston of a vacuum device from an extended position to a retracted position, the piston forming a portion of the sealed region.

* * * * *